United States Patent [19]

Merger et al.

[11] 4,243,815

[45] Jan. 6, 1981

[54] PREPARATION OF METHYLENE-BIS(4-PHENYLCARBAMIC ACID ESTERS)

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 114,362

[22] Filed: Jan. 22, 1980

[30] Foreign Application Priority Data

Feb. 9, 1979 [DE] Fed. Rep. of Germany ....... 2904917

[51] Int. Cl.$^3$ ........................................... C07C 125/07
[52] U.S. Cl. ...................................................... 560/25
[58] Field of Search ........................................... 560/25

[56] References Cited

U.S. PATENT DOCUMENTS

| 2,946,768 | 7/1960 | Klauke et al. | 560/25 |
| 3,467,694 | 9/1969 | Hardy et al. | 560/25 |
| 3,584,000 | 6/1971 | Hobart et al. | 560/25 |
| 3,751,370 | 8/1973 | Stemberg et al. | 560/25 |
| 3,992,430 | 11/1976 | Bacskai | 560/25 |
| 4,081,472 | 3/1978 | Tsumura et al. | 260/453 P |
| 4,146,727 | 3/1979 | Shawl et al. | 560/25 |
| 4,163,019 | 7/1979 | Mango | 560/25 |

Primary Examiner—Natalie Trousof
Assistant Examiner—G. T. Breytenstein
Attorney, Agent, or Firm—Keil & Witherspoon

[57] ABSTRACT

A process for the preparation of methylene-bis-(4-phenylcarbamic acid esters), wherein an N-phenylcarbamic acid ester is reacted with a formaldehyde-acetal in the presence of an acid at up to 200° C.

6 Claims, No Drawings

PREPARATION OF METHYLENE-BIS(4-PHENYLCARBAMIC ACID ESTERS)

The present invention relates to a novel process for the preparation of methylene-bis-(4-phenylcarbamic acid esters) by reacting an N-phenylcarbamic acid ester with a formaldehyde-acetal.

Methylene-bis-(4-phenylcarbamic acid esters) are valuable starting materials for the preparation of methylene-bis-(4-phenylisocyanates), which are conventionally used for the preparation of polyurethanes (cf. German Laid-Open Application DOS No. 2,635,490).

To prepare the methylene-bis-(4-phenylcarbamic acid esters), aniline is condensed with formaldehyde in the presence of hydrochloric acid and the resulting methylene-bis-(4-aniline) is reacted with a chloroformic acid ester in the presence of a base, or methylene-bis-(4-aniline) and phosgene are reacted to give methylene-bis-(4-phenylisocyanate), which is then reacted with the appropriate alcohol.

This process has the disadvantage that when condensing aniline with formaldehyde oligomer and isomer mixtures are formed to a large degree, and that the reaction with phosgene requires a complicated technique, for safety reasons. Furthermore, the hydrochloric acid required for the preparation of methylene-bis-(4-aniline), and the hydrochloric acid additionally produced during the subsequent reaction, pollute the environment.

Methylene-bis-(4-phenylcarbamic acid esters) can also be prepared by reacting methylene-bis-(4-nitrophenyl) with an alcohol and carbon monoxide (cf. German Published Application DAS No. 1,568,044). Since the preparation of the nitro compound required for this reaction presents great difficulties, the process has not attained any industrial significance.

We have found that methylene-bis-(4-phenylcarbamic acid esters) are obtained in a particularly advantageous manner and in excellent yields when an N-phenylcarbamic acid ester is reacted with a formaldehyde-acetal in the presence of an acid at up to 200° C.

In the case of methylene-bis-(4-phenylcarbamic acid methyl ester) the reaction can be represented by the following equation:

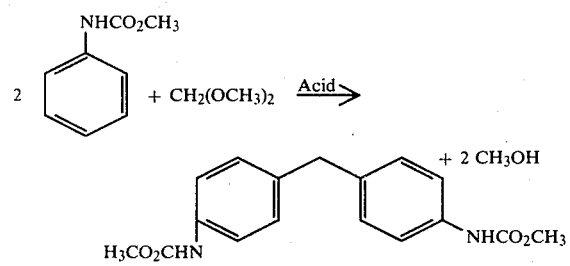

Examples of suitable N-phenylcarbamic acid esters are compounds of the formula

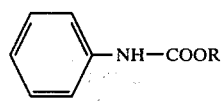

where R is alkyl of 1 to 4 carbon atoms and the phenyl radical may be substituted by methyl in the o- and/or m-positions.

Accordingly, suitable N-phenylcarbamic acid esters include methyl, ethyl, propyl and butyl N-phenylcarbamate, methyl and ethyl N-o-tolylcarbamate, methyl and ethyl N-2,6-dimethylphenylcarbamate and methyl N-m-tolylcarbamate.

Examples of suitable formaldehyde-acetals are compounds of the formula

where R is alkyl of 1 to 4 carbon atoms. Preferred acetals are those where the alkyl radical is the same as the radical of the alkanol from which the carbamic acid ester has been formed.

The preparation, in accordance with the invention, of methylene-bis-(4-phenylcarbamic acid esters) from methyl or ethyl N-phenylcarbamate and formaldehyde dimethylacetal or diethylacetal is of particular industrial importance.

The reaction of the starting materials is carried out in the presence of an acid, at up to 200° C., preferably at from 50° to 150° C., especially at from 70° to 130° C., and with a molar ratio of carbamic acid ester to acetal of, for example, from 1:1 to 1:0.1, preferably from 1:0.6 to 1:0.2.

Examples of suitable acids are phosphoric acid, sulfuric acid, alkylsufonic acids, eg. methanesulfonic acid, or arylsulfonic acids, eg. p-toluenesulfonic acid. These acids are used, for example, in amounts of from 1 to 100, preferably from 10 to 60, mol %, based on carbamic acid ester. In a particularly advantageous embodiment of the invention, a strong acid which can be separated from the reaction mixture by distillation, for example trifluoromethanesulfonic acid, is used. In this way, working up the reaction mixture with water or with a base can be avoided and the acid can be directly recycled to the reaction.

In a further advantageous embodiment of the invention, the acid used is a strongly acid organic cation exchanger, for example an exchange resin containing sulfonic acid groups. These ion exchangers are either suspended in the reaction mixture, or arranged as a fixed bed, in each case using conventional methods.

The process according to the invention is preferably carried out with water substantially or in particular completely absent, ie. using acids which are virtually anhydrous. The reaction may be carried out in the absence of a solvent or in the presence of a non-aqueous solvent, eg. benzene, methylcyclohexane, acetic acid, methanol, methyl acetate, nitrobenzene, chlorobenzene, dichlorobenzene or an aliphatic chlorohydrocarbon.

The reaction, which is complete after from about 0.5 to 20 hours, is in general carried out either by slowly adding the acetal to a mixture of the carbamic acid ester and the acid at the reaction temperature, whilst stirring, or by heating a mixture of the carbamic acid ester, the acetal and the acid, whilst stirring, and in each case keeping the mixture for an appropriate time at the reaction temperature. The reaction product is isolated by conventional methods, for example by extracting the acid with water. Any solvent present, and unconverted starting materials, are removed by distillation under reduced pressure.

The condensation of the phenylcarbamic acid ester with the formaldehyde derivative in question can be carried out in individual batches or as a continuous process.

An essential difference between the process according to the invention and the processes of U.S. Pat. No. 2,946,768 and German Laid-Open Application DOS No. 2,832,379, in which formaldehyde of formaldehyde donors are used, so that there is always water present in the reaction mixture, is that in the process according to the invention no formaldehyde, and hence no water of reaction, is formed. Accordingly, hydrolysis of the carbamic acid esters to amines, formation of ureas, and the consequent pollution of the effluent, are avoided.

EXAMPLE 1 (COMPARATIVE EXAMPLE)

Following the procedure of Example 2 of German Pat. No. 1,042,891, a mixture of 183 parts of methyl phenylcarbamate, 500 ml of water and 86 parts of 30% strength formaldehyde solution is heated to 100° C., whilst stirring. 100 ml of concentrated hydrochloric acid are then added. Thereafter the reaction mixture is stirred for 20 hours at 100° C. After completion of the reaction, the aqueous phase is separated off. The reaction product is washed three times with hot water and unconverted starting material is then distilled off under reduced pressure. The residue is analyzed by means of high pressure liquid chromatography (HPLC). It contains 50% of methylene-bis-(phenylcarbamic acid methyl ester), 9% of a tricyclic product, 16% of N-C-linked bicyclic product and 10% of N-C-linked tricyclic product. The remainder consists of polycyclic compounds not identified in more detail.

EXAMPLE 2 (COMPARATIVE EXAMPLE)

A mixture of 90 parts of methyl phenylcarbamate, 250 ml of chlorobenzene and 40 parts of 30% strength formaldehyde solution is heated to 100° C. whilst stirring, and 50 ml of concentrated hydrochloric acid are then added. Thereafter the reaction mixture is stirred for 20 hours at 100° C. After completion of the reaction, the aqueous phase is separated off and washed twice with water. The chlorobenzene and unconverted starting material are then distilled off. According to HPLC analysis, the residue contains 49% of methylene-bis-(phenylcarbamic acid methyl ester), 12% of tricyclic product, 15% of N-C-linked bicyclic product and 9% of N-C-linked tricyclic product. The remainder consists of polycyclic compounds not identified in more detail.

EXAMPLE 3

A mixture of 151 parts of methyl phenylcarbamate, 38 parts of dimethylformal, 120 parts of nitrobenzene and 50 parts of ®LEWATIT SPC-108 is heated to 120° C. in a stirred autoclave, and kept at this temperature for 15 hours, with the stirrer running throughout. After completion of the reaction, the catalyst is separated off. Nitrobenzene and unconverted starting material are then distilled off under reduced pressure. 142 parts of a distillation residue are obtained; according to HPLC analysis, this consists of 56% of methylene-bis-(phenylcarbamic acid methyl ester), 23% of tricyclic product and 21% of polycyclic products.

LEWATIT SPC-108 is a commercially available macroporous cation exchanger based on a copolymer of styrene and 8% of divinylbenzene and containing sulfonic acid groups; it has a particle size of 0.3–1.5 mm, a total capacity of about 4.2 milliequivalents/g of solids, a pore surface area of about 20 m$^2$/g (measured by the BET method) and a mean pore diameter of about 500 Å (measured by the BET method).

EXAMPLE 4

A mixture of 227 parts of methyl phenylcarbamate, 38 parts of dimethylformal and 60 parts of LEWATIT SC-104 is heated to 120° C. in a stirred autoclave, and kept at this temperature for 15 hours, with the stirrer running throughout.

After completion of the reaction, the catalyst is separated off. Unconverted starting material is then distilled off under reduced pressure. 136 parts of a distillation residue are obtained; according to HPLC analysis, this consists of 68% of methylene-bis-(phenylcarbamic acid methyl ester), 20% of tricyclic product and 12% of polycyclic products.

LEWATIT SC-104 is a commercially available gel-like cation exchanger based on a copolymer of styrene and 4% of divinylbenzene and containing sulfonic acid groups; it has a particle size of 0.3–1.2 mm and a total capacity of about 4.2 milliequivalents/g of solids.

EXAMPLE 5

A mixture of 151 parts of methyl phenylcarbamate, 38 parts of dimethylformal, 110 parts of chlorobenzene and 20 parts of trifluoromethanesulfonic acid is heated to 100° C. in a stirred autoclave, and kept at this temperature for 10 hours, with the stirrer running throughout. After completion of the reaction, the catalyst, the solvent and the unconverted starting material are distilled off under reduced pressure.

150 parts of a distillation residue are obtained; according to HPLC analysis, this consists of 52% of methylene-bis-(phenylcarbamic acid methyl ester), 30% of tricyclic product and 18% of polycyclic products.

EXAMPLE 6

A mixture of 375 parts of methyl phenylcarbamate, 150 parts of nitrobenzene, 38 parts of dimethylformal and 30 parts of concentrated sulfuric acid is heated to 100° C. is a stirred autoclave, and kept at this temperature for 15 hours, with the stirrer running throughout. After the reaction has been completed, and the acid has been extracted with water, the solvent and unconverted starting material are distilled off under reduced pressure. The distillation residue is recrystallized from toluene. 110 parts of methylene-bis-(4-phenylcarbamic acid methyl ester) are obtained.

EXAMPLE 7

A suspension of 151 parts (1 mole) of methyl N-phenylcarbamate, 38 parts (0.5 mole) of formaldehyde dimethylacetal and 30 g of a cation exchanger which is commercially available under the name LEWASORB AC 10, contains sulfonic acid groups and has a particle size of from 10 to 200 μm, is heated to 80° C. in a stirred reactor, and kept at this temperature for two hours, with the stirrer running throughout. Before use, the catalyst is dried for 20 hours at 100° C. under reduced pressure. After completion of the reaction, the catalyst is filtered off and the unconverted starting materials are distilled off. Recrystallization of the residue from toluene gives 114 parts of pure methylene-bis-(4-phenylcarbamic acid methyl ester), ie. 73% of theory.

EXAMPLE 8

A suspension of 330 parts (2 moles) of ethyl N-phenylcarbamate, 45 parts (0.5 mole) of formaldehyde diethylacetal and 50 g of a cation exchanger which is commercially available under the name LEWASORB AC 10, contains sulfonic acid groups and has a particle size of from 10 to 200 μm, is heated to 100° C. in a stirred autoclave, and kept at this temperature for two hours, with the stirrer running throughout. Before use, the catalyst is dried for 20 hours at 100° C. under reduced pressure. After completion of the reaction, the catalyst is filtered off and the unconverted starting materials are distilled off. Recrystallization of the residue from toluene gives 150 parts of pure methylene-bis-(4-phenylcarbamic acid ethyl ester), ie. 80% of theory.

We claim:

1. A process for the preparation of methylene-bis-(4-phenylcarbamic acid esters), wherein a N-phenylcarbamic acid ester is reacted with a formaldehyde-acetal in the presence of an acid at up to 200° C.

2. A process as claimed in claim 1, wherein the N-phenylcarbamic acid ester used is a compound of the formula

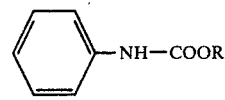

where R is alkyl of 1 to 4 carbon atoms and the phenyl radical may be subsituted by methyl in the o- and/or m-positions.

3. A process as claimed in claim 1, wherein a formaldehyde-acetal of the formula $CH_2(OR)_2$ where R is alkyl of 1 to 4 carbon atoms, is used.

4. A process as claimed in claim 1, wherein methyl N-phenylcarbamate or ethyl N-phenylcarbamate is reacted with formaldehyde-dimethylacetal or formaldehyde-diethylacetal.

5. A process as claimed in claim 1, wherein trifluoromethanesulfonic acid is used as the acid.

6. A process as claimed in claim 1, wherein a strongly acid cation exchanger is used as the acid.

* * * * *